United States Patent
Dugand et al.

(10) Patent No.: US 11,285,270 B2
(45) Date of Patent: Mar. 29, 2022

(54) INJECTION DEVICE HAVING AN IMPROVED SYRINGE CAP REMOVAL

(71) Applicant: Nemera La Verpillière, La Verpilliere (FR)

(72) Inventors: Pascal Dugand, Estrablin (FR); Kevin Stamp, Sheffield (GB)

(73) Assignee: Nemera La Verpillière

(*) Notice: Subject to any disclaimer, the term of this patent is extended or adjusted under 35 U.S.C. 154(b) by 239 days.

(21) Appl. No.: 16/463,720

(22) PCT Filed: Oct. 18, 2017

(86) PCT No.: PCT/FR2017/052865
§ 371 (c)(1),
(2) Date: May 23, 2019

(87) PCT Pub. No.: WO2018/096231
PCT Pub. Date: May 31, 2018

(65) Prior Publication Data
US 2019/0374727 A1    Dec. 12, 2019

(30) Foreign Application Priority Data

Nov. 23, 2016 (FR) ..................................... 1661383

(51) Int. Cl.
*A61M 5/32* (2006.01)
*A61M 5/20* (2006.01)

(52) U.S. Cl.
CPC ... *A61M 5/3204* (2013.01); *A61M 2005/2006* (2013.01); *A61M 2205/586* (2013.01)

(58) Field of Classification Search
CPC .................................................. A61M 5/3204
See application file for complete search history.

(56) References Cited

U.S. PATENT DOCUMENTS

2016/0089495 A1    3/2016   Julian et al.
2016/0220765 A1    8/2016   Julian et al.
(Continued)

FOREIGN PATENT DOCUMENTS

EP      2745866 A1    6/2014
EP      2878322 A1    6/2015
(Continued)

OTHER PUBLICATIONS

International Search Report for PCT/FR2017/052865 dated Dec. 7, 2017.

*Primary Examiner* — Emily L Schmidt
(74) *Attorney, Agent, or Firm* — St. Onge Steward Johnston & Reens LLC (57) ABSTRACT

An assistance device for assisting in operation of an injection syringe including a syringe body carrying an injection needle covered with a protective cap. The assistance device includes a support for housing the syringe body, and a removal device for removing the protective cap, having a gripping member to be maneuvered by a user to remove this protective cap from the injection needle, and at least one extractor cooperating with the protective cap during removal of the protective cap. The removal device also has complementary members for controlling the extractor, which can be moved relative to each other in a relative engagement movement, to move the extractor between a reference configuration retracted relative to the protective cap and a cooperation configuration cooperating with the protective cap. The relative engagement movement is independent of the maneuvering movement applied by the user to the gripping member to remove the protective cap.

11 Claims, 10 Drawing Sheets

(56) References Cited

U.S. PATENT DOCUMENTS

2017/0354789 A1* 12/2017 Bendek ............... A61M 5/3204
2017/0361030 A1* 12/2017 Moore ................ A61M 5/3202

FOREIGN PATENT DOCUMENTS

| GB | 2438593 A | 12/2007 |
| WO | 2014091153 A1 | 6/2014 |
| WO | 2015044561 A1 | 4/2015 |
| WO | 2015110532 A1 | 7/2015 |
| WO | 2016193374 A1 | 12/2016 |

* cited by examiner

INJECTION DEVICE HAVING AN IMPROVED SYRINGE CAP REMOVAL

FIELD OF THE INVENTION

This invention relates to injection assemblies comprising an assistance device for assisting in the operation of an injection syringe and an injection syringe housed in this assistance device.

BACKGROUND OF THE INVENTION

In the medical field, for example, an injection syringe is used to inject a liquid medication into the body of a patient. The injection syringe generally comprises a syringe body carrying an injection needle, a piston housed in the syringe body defining a chamber containing the medication to be injected, and a rod for maneuvering this piston.

Frequently, a third party injects the medication into the body of the patient using a syringe containing this medication.

However, the possibility of the third party accidentally pricking himself with the syringe needle when handling the syringe must be avoided whenever possible.

In the state of the art, for example in accordance with the description of WO 2015/044561, a first type of assistance device for assisting in the operation of an injection syringe preventing or limiting accidents when handling a syringe has therefore been developed, for example by automatically masking the syringe needle, just after injection.

Sometimes, the patient himself performs the injection on a part of his body. This is the case, for example, for patients suffering from rheumatoid arthritis, multiple sclerosis, diabetes or undergoing an anaphylactic shock in case of allergy.

SUMMARY OF THE INVENTION

In this case, as when the injection is performed by a third party, the possibility of the patient accidentally pricking himself with the syringe needle when handling the syringe must be avoided whenever possible. However, the syringe must also be easy to maneuver since the patient performing the injection himself may be weakened or feel a certain degree of apprehension in performing the injection.

In the state of the art, a second type of assistance device for assisting in the operation of an injection syringe preventing, as in the previous case, accidents when handling the syringe, but also automating some of the syringe operation steps, especially insertion of the syringe needle into the body of the patient and insertion of the syringe piston into the syringe body, has therefore been developed.

The above-mentioned assistance devices for assisting in the operation of an injection syringe generally comprise a syringe support in which the pre-filled syringe is housed. Before use, the syringe injection needle is covered with a removable protective cap. To prevent a handling accident as soon as the cap has been removed by the user, the above-mentioned assistance devices for assisting in the operation of an injection syringe generally comprise a cap removal device removably connected to the syringe support, in order to remove the cap under good safety conditions. Such a cap removal device, described for example in WO 2015/044561, comprises:
  a gripping member, intended to be manoeuvred by a user in order to remove the cap from the needle, and
  extractors cooperating with the cap when removing the cap.

Before use, the cap removal device is removably connected to the syringe support.

The assistance device described in WO 2015/044561 comprises first and second complementary control members for controlling each extractor which can be moved relative to each other in a relative cooperation movement, known as a relative engagement movement. This relative engagement movement moves each extractor between a reference configuration retracted relative to the cap and a cooperation configuration cooperating with the cap.

The first and second complementary control members described in WO 2015/044561 are carried respectively by the syringe support and by the gripping member.

Before being removed, the needle protective cap is kept inserted on a complementary part of the syringe body, by friction.

In addition, the relative engagement movement acts against the frictional sources, in particular between the complementary extractor control members.

Lastly, in the assistance device described in WO 2015/044561, the relative engagement movement is coupled with the manoeuvring movement applied by the user to the gripping member in order to remove the cap from the needle.

Consequently, in WO 2015/044561, due to this coupling of movements, the manoeuvring movement applied by the user to the gripping member in order to remove the cap from the needle acts against:
  firstly, the frictional forces between the complementary extractor control members, and
  secondly, the frictional forces keeping the protective cap inserted on a complementary part of the syringe body.

However, it is generally imposed that the force required in order to remove the protective cap from the needle should be relatively low so that the user can remove the cap easily.

In WO 2015/044561, since the maneuvering movement applied by the user to the gripping member in order to remove the cap from the needle acts against both the frictional sources between the complementary extractor control members and the frictional forces keeping the protective cap inserted, it is difficult to respect the force limit imposed for easy removal of the cap by a user.

In addition, each extractor generally consists of an elastic arm extending substantially longitudinally in a generally sleeve-shaped part of the gripping member. This elastic arm forms a lever deformable between the extractor retracted reference and cooperation configurations. A resistance end of the lever, in the shape of a hook, is intended, during the maneuvering movement applied by the user to the gripping member in order to remove the cap from the needle, to engage with an end edge of the cap. In some cases, however, this end edge of the cap is not sufficiently removed and the extractor may not engage with the cap when it is pulled by the maneuvering movement applied by the user to the gripping member in order to remove the cap from the needle.

The invention aims to provide an assistance device for assisting in the operation of an injection syringe fitted with a cap removal device that is easy to handle, in other words requiring only a limited force by a user to remove the cap.

The invention therefore relates to an assistance device for assisting in the operation of an injection syringe comprising a syringe body carrying an injection needle covered with a removable protective cap, the assistance device comprising:
  a syringe support in which the syringe body is intended to be housed, and
  a removal device for removing the protective cap removably connected to the syringe support, comprising:

a gripping member, intended to be manoeuvred by a user in order to remove this protective cap from the injection needle, and at least one extractor cooperating with the protective cap when removing the protective cap, characterised in that the removal device comprises first and second complementary control members for controlling the extractor which can be moved relative to each other in a relative cooperation movement, known as a relative engagement movement, in order to move the extractor between a reference configuration retracted relative to the protective cap and a cooperation configuration cooperating with the protective cap, the relative engagement movement being independent of the maneuvering movement applied by the user to the gripping member in order to remove the protective cap from the injection needle.

Since the relative engagement movement is independent of the maneuvering movement applied by the user to the gripping member in order to remove the cap from the needle, these two movements can be carried out at different times.

Thus, the relative engagement movement moving the extractor between its reference configuration retracted relative to the cap and its cooperation configuration cooperating with the cap can be carried out during a step of assembling the assistance device for assisting in the operation of the injection syringe or during a step of assembling an injection assembly comprising this assistance device and an injection syringe housed in this assistance device.

During the assembly, it will be possible to check that the extractor is engaged with the cap. The injection assembly comprising the assistance device and the injection syringe housed in this assistance device will therefore be delivered to the user with an extractor engaged with the cap, even before the user maneuvers the gripping member in order to remove the cap from the needle.

Subsequently, when the user maneuvers the gripping member in order to remove the cap from the needle, he will only have to apply a force sufficient to overcome the frictional forces keeping the protective cap inserted on the complementary part of the syringe body.

Thanks to the invention therefore, the cap can be easily and safely removed by a user.

According to other optional characteristics of the assistance device for assisting in the operation of the injection syringe and various embodiments of the invention:

the gripping member comprises a generally sleeve-shaped proximal part, the extractor consisting of an elastic arm extending substantially longitudinally in the proximal part and forming a class 3 lever deformable between the retracted reference and cooperation configurations, the extractor being provided with a so-called resistance end, intended to cooperate with the protective cap;

the removal device comprises at least two extractors forming respectively two class 3 levers, substantially parallel to each other, these extractors each being provided with a so-called resistance end, intended to cooperate with the protective cap, and a so-called support end opposite the resistance end, the support ends of the extractors being connected together;

the maneuvering movement applied by the user to the gripping member in order to remove the protective cap from the injection needle comprises a translation, the relative engagement movement being parallel to this translation;

the first and second complementary control members for controlling the extractor cooperate with each other by ramp effect under the effect of the relative engagement movement;

the first and second complementary control members for controlling the extractor are carried respectively by the gripping member and by the extractor;

the extractor is carried by a slide mounted slidably in translation in the gripping member, the first and second complementary control members for controlling the extractor being attached respectively in translation to the gripping member and to the extractor;

the first control member for controlling the extractor is formed on an inner surface of the proximal part and the second control member for controlling the extractor is formed on the extractor;

the syringe support and the slide comprise complementary stops for positioning the extractor in its reference configuration retracted relative to the protective cap;

the gripping member and the slide comprise complementary means for coupling to each other allowing the relative engagement movement between them;

the gripping member and the slide comprise complementary means for locking to each other that can be activated at the end of the relative engagement movement;

the extractor is attached to the gripping member, the first control member for controlling the extractor being carried by a maneuvering member mounted slidably in translation in the gripping member and the second control member for controlling the extractor being attached in translation to the extractor;

the gripping member and the syringe support comprise complementary stops for positioning the extractor in its reference configuration retracted relative to the protective cap;

the gripping member and the syringe support comprise complementary means for locking to each other that can be released when starting the maneuvering movement applied by the user to the gripping member in order to remove the protective cap from the injection needle;

the syringe support comprises an outer body of generally tubular shape and an end sleeve projecting from one end of this outer body, the stop carried by the syringe support to position the extractor in its reference configuration retracted relative to the protective cap being formed on the end of the outer body, and the complementary means for locking the gripping member and the syringe support being formed on the gripping member and the end sleeve;

the gripping member and the maneuvering member carrying the first control member for controlling the extractor comprise complementary means for locking to each other that can be released when starting the relative engagement movement;

the gripping member and the maneuvering member carrying the first control member for controlling the extractor comprise complementary means for locking to each other that can be activated at the end of the relative engagement movement.

The invention also relates to an injection assembly comprising an assistance device for assisting in the operation of an injection syringe and an injection syringe housed in this assistance device, characterised in that the assistance device for assisting in the operation of the injection syringe is according to the invention.

BRIEF DESCRIPTION OF THE DRAWINGS

The invention will be better understood on reading the following description, given solely by way of example and with reference to the accompanying drawings in which.

DETAILED DESCRIPTION OF THE INVENTION

FIGS. 1 to 10 show an injection assembly 22 of very general shape of revolution about an axis X.

The injection assembly 22 comprises an assistance device 24 for assisting in the operation of an injection syringe according to a first embodiment of the invention. The injection assembly 22 also comprises an injection syringe 26 (shown in particular on FIGS. 2, 4 and 7) housed in this assistance device 24.

In the example shown, the injection syringe 26 can be used to inject a liquid medication into the body of a patient.

Figure 7:
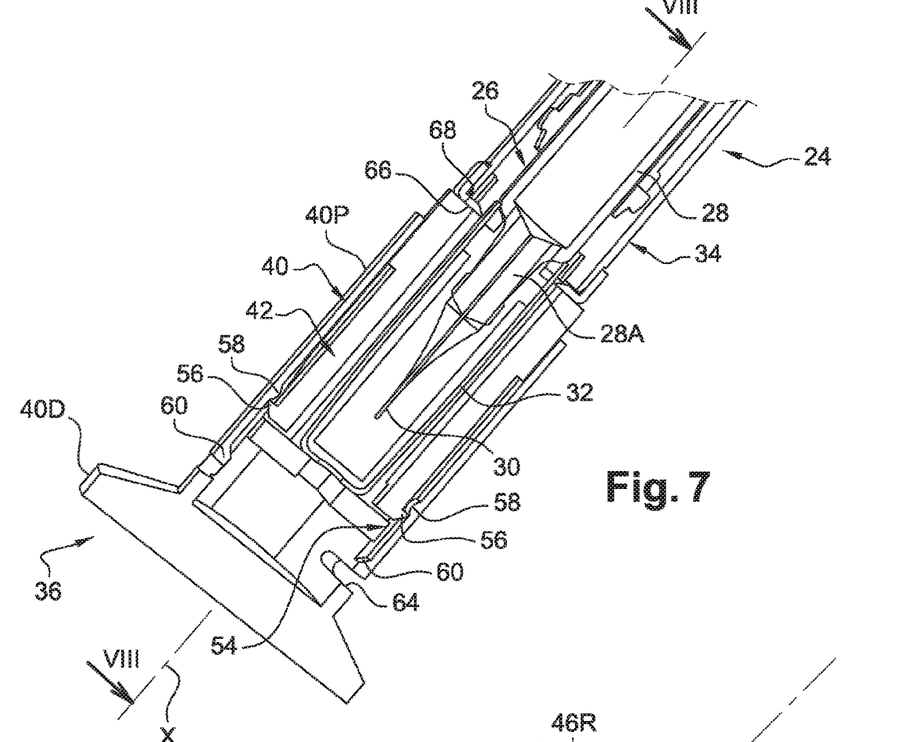
FIG. 7 is a cross-sectional view, along line VII-VII of FIG. 3, of a distal part of the device shown on the previous figures.
Figure 8:
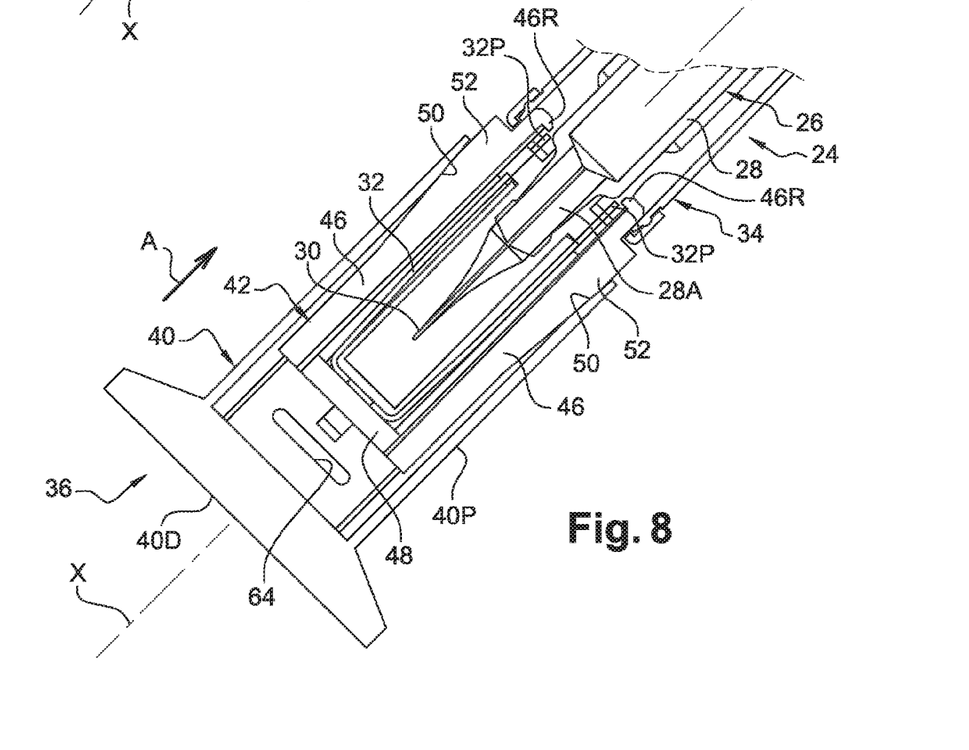
FIG. 8 is a cross-sectional view, along line VIII-VIII of FIG. 7, of the distal part of the device shown on the previous figures.

As shown in particular on FIGS. 7 and 8, the injection syringe 26 comprises, traditionally, a syringe body 28 carrying an injection needle 30. Before using the injection assembly 22, the injection needle 30 is covered with a removable protective cap 32. This protective cap 32, covering the injection needle 30, is kept inserted on a complementary part 28A of the syringe body 28, by friction.

The injection syringe 26 also comprises a piston (not shown) housed in the syringe body 28 and defining a chamber containing the medication to be injected. The piston is traditionally connected to a maneuvering rod.

The assistance device 24 is of the type described in WO 2015/044561. It prevents or limits accidents when handling the injection syringe 26, for example by automatically masking the injection needle 30 of the injection syringe 26, just after the injection.

In the remainder of this document, a component of the assistance device 24 will be qualified as proximal or distal depending on whether it is close to or away from the hand of the user actuating this assistance device 24, when the user injects a medication using the assistance device 24.

As can be seen in particular on FIGS. 1 to 4, 7 and 8, the assistance device 24 comprises a syringe support 34, comprising a set of traditional components, in which the syringe body 28 is housed.

The assistance device 24 also comprises a removal device 36 for removing the protective cap 32. This removal device 36 is removably connected to the syringe support 34.

As can be seen in particular on FIGS. 7 to 10, the removal device 36 for removing the protective cap 32 comprises a gripping member 40, intended to be maneuvered by a user to remove this protective cap 32 from the injection needle 30, and a slide 42 mounted slidably in translation, substantially parallel to the axis X, in the gripping member 40.

The gripping member 40 and the slide 42 are preferably made of plastic.

Figure 1:
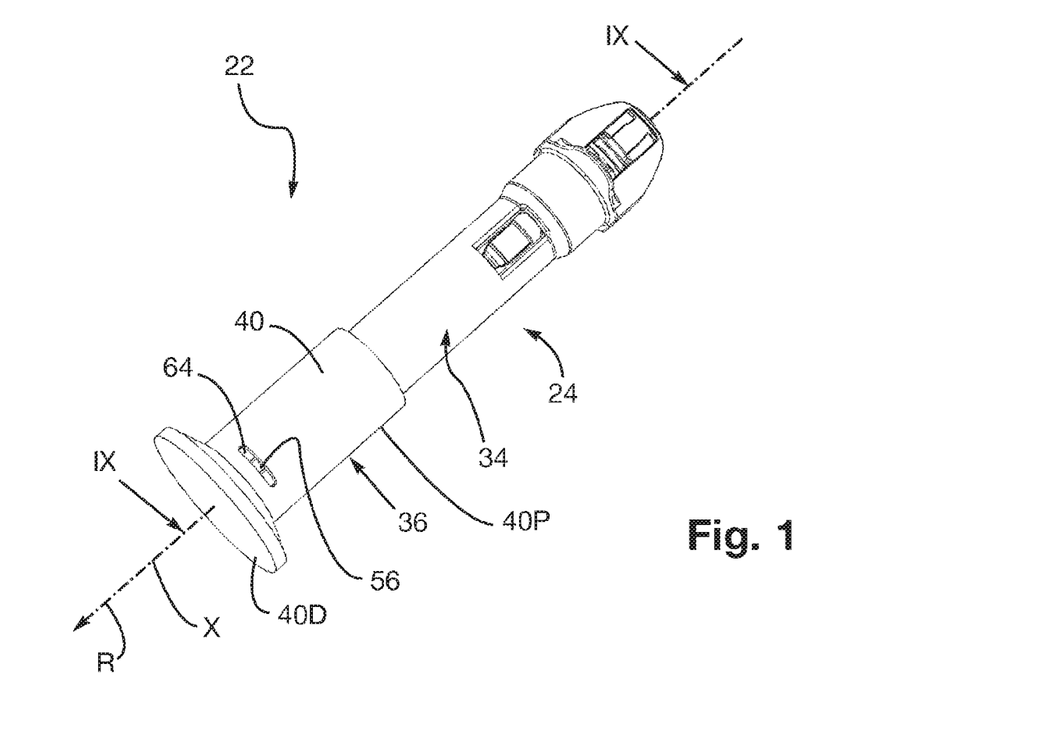
FIGS. 1 to 4 are perspective views of an injection assembly comprising an assistance device for assisting in the operation of an injection syringe according to a first embodiment of the invention, in various use or assembly configurations.

Preferably, the maneuvering movement applied by the user to the gripping member 40 in order to remove the protective cap 32 from the injection needle 30 corresponds to a translation, substantially parallel to the axis X, made in the proximal to distal direction shown by the arrow R on FIG. 1.

Figure 3:
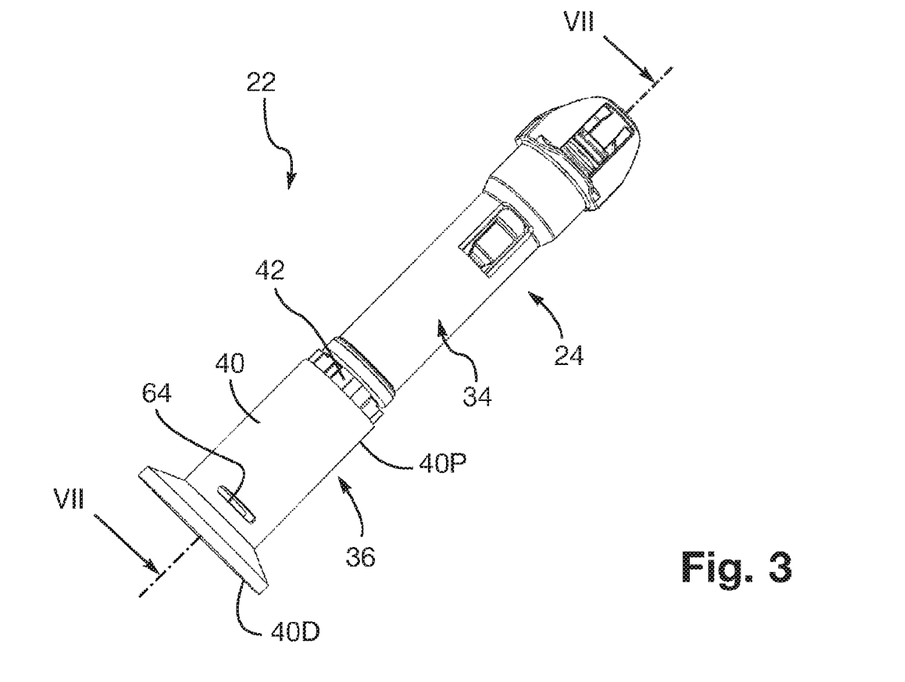
Figure 5:
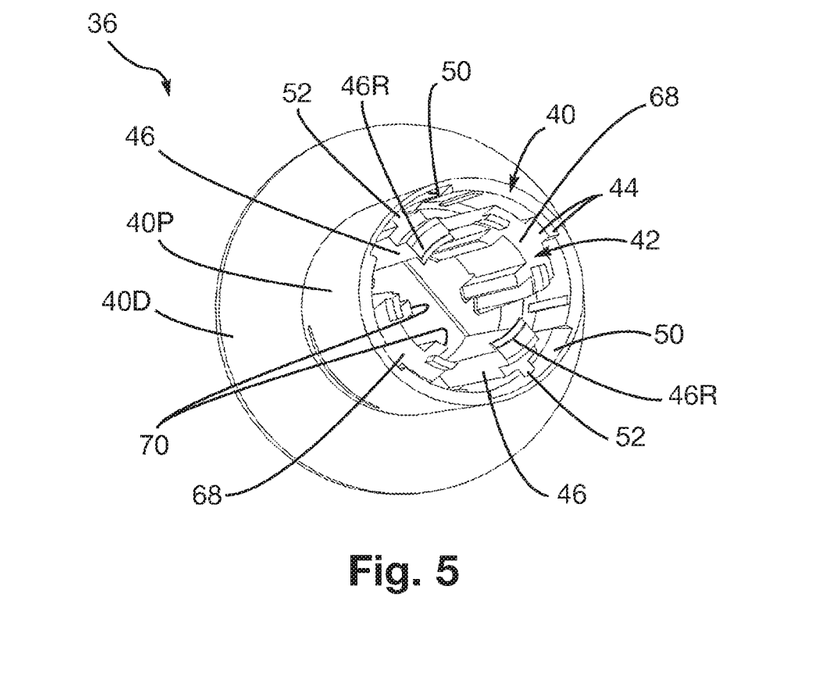
FIG. 5 is a perspective view of a protective cap removal device, fitted to the assistance device for assisting in the operation of an injection syringe illustrated on the previous figures.

Referring in particular to FIGS. 1, 3 and 5, we see that the gripping member 40 comprises a generally sleeve-shaped proximal part 40P, extended by a distal head 40D whose outer surface flares in the proximal to distal direction. The slide 42 is mounted slidably in translation in the proximal part 40P of the gripping member 40.

The gripping member 40 and the slide 42 comprise complementary means 44 for relative guiding in translation (shown on FIGS. 5 and 6), for example of tab and groove type.

In addition, the slide 42 comprises two substantially parallel extractors 46, intended to cooperate with the protective cap 32 when removing this protective cap 32.

More particularly, the two extractors 46 are intended to cooperate with two diametrically opposed parts of the proximal part 40P.

As an alternative, the slide 42 could comprise only a single extractor 46 or more than two extractors 46, for example three.

As will be described in more detail below, each extractor 46 is intended to move between a reference configuration retracted relative to the protective cap 32 and a cooperation configuration cooperating with this protective cap 32.

Each extractor 46 consists of an elastic arm extending substantially longitudinally in the proximal part 40P. Each extractor 46 is returned elastically to a rest state which corresponds to its retracted reference configuration.

Note that three lever classes are generally identified according to the relative positions of the fulcrum (about which the lever pivots) and the points where the effort and the load are applied.

Preferably, each extractor 46 forms a class 3 lever deformable between the retracted reference and cooperation configurations. Thus, firstly, each extractor 46 is provided with a so-called resistance end 46R, for example in the shape of a hook, intended to cooperate with a proximal end edge 32P of the protective cap 32. As an alternative, the resistance end 46R of each extractor 46 could cooperate with another surface of the protective cap 32. Thus, when the injection syringe carries a protective cap provided with lateral windows, the extractors are designed so that the resistance end of at least one of the extractors is inserted in one of the windows so as to grip (cooperate with) the edge of this window in cooperation configuration. According to another embodiment, not shown, the extractors are designed shorter than the protective cap, the inner surface of each extractor being provided with a gripping surface intended, in cooperation configuration, to grip the protective cap by friction. The gripping surface may be smooth, have a relief or a surface state designed to increase the friction. Secondly, each extractor 46 is provided with a so-called support end 46A, opposite the resistance end 46R, made in one piece with a base 48 forming a distal end of the slide 42 (see in particular FIGS. 6 and 8). Thus, the support ends 46A of the extractors 46 are connected to each other by the base 48 of the slide 42.

For each extractor 46, the removal device 36 comprises first 50 and second 52 complementary control members for controlling the extractor 46 (see in particular FIGS. 5, 6, 8 and 10) which can be moved relative to each other in a relative cooperation movement, known as a relative engagement movement. The relative engagement movement is independent of the maneuvering movement applied by the user to the gripping member 40 when removing the protective cap 32 from the injection needle 30. More particularly, the relative engagement movement is parallel to the translation movement applied by the user when maneuvering the gripping member 40 in order to remove the protective cap 32 from the injection needle 30. However, considering the support 34 and the slide 42 to be fixed, the relative engagement movement is made by moving the gripping member 40 in the direction opposite to that shown by the arrow R on FIG. 1. The direction of the relative engagement movement, under the above-mentioned conditions, is shown by the arrow A on FIG. 8.

Preferably, the first 50 and second 52 complementary control members for controlling the extractor 46 cooperate with each other by ramp effect under the effect of the relative engagement movement. Thus, referring in particular to FIGS. 5 and 6, we see that, for each extractor 46, the first control member consists of a recess 50 formed on an inner surface of the proximal part 40P of the gripping member 40. In addition, for each extractor 46, the second control member consists of a radial projection 52 forming a ramp formed on the extractor 46.

Due to this arrangement, for each extractor 46, the first 50 and second 52 complementary control members for controlling this extractor 46 are carried respectively by the gripping member 40 and by the extractor 46. More particularly, these first 50 and second 52 control members are attached respectively in translation to the gripping member 40 and to the extractor 46.

Referring more particularly to FIG. 7, we see that the gripping member 40 and the slide 42 comprise complementary means 54 for coupling to each other allowing the relative engagement movement between this gripping member 40 and the slide 42.

These complementary coupling means 54 comprise for example, as shown on FIG. 7, a pair of coupling lugs 56 substantially diametrically opposed relative to the axis X, trapped axially between two respectively proximal 58 and distal 60 coupling gadroons formed on the inner surface of the generally sleeve-shaped proximal part 40P of the gripping member 40. The coupling lugs 56 can be moved axially between the proximal 58 and distal 60 gadroons in order to allow the relative engagement movement of the first 50 and second 52 control members for controlling each extractor 46.

Figure 9:
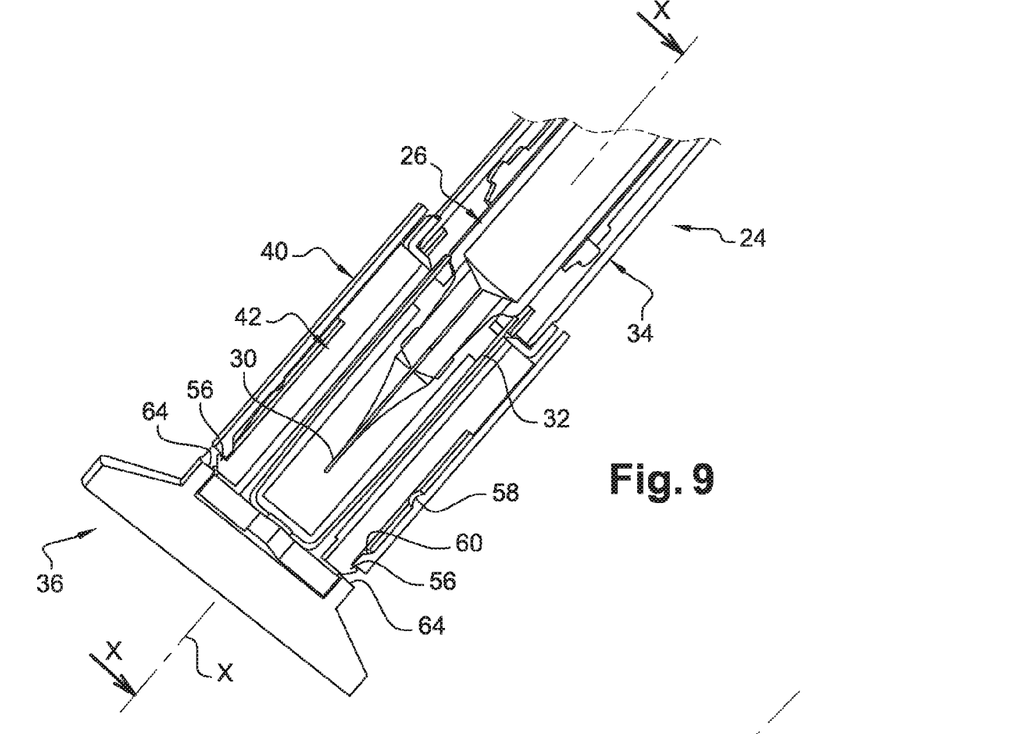
FIG. 9 is a cross-sectional view, along line IX-IX of FIG. 1, of the distal part of the device shown on the previous figures.
Figure 10:
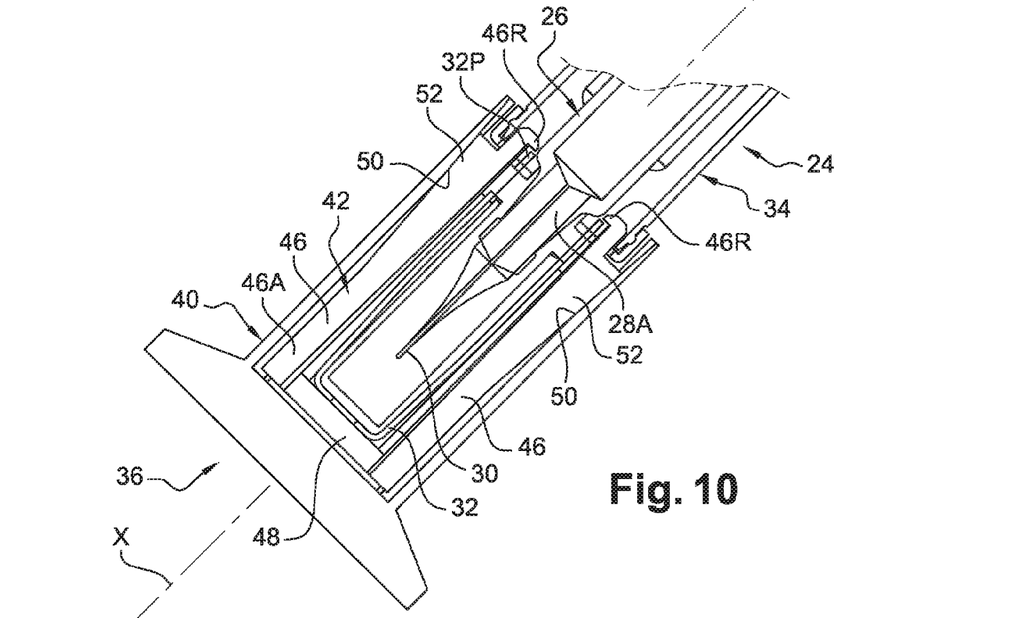
FIG. 10 is a cross-sectional view, along line X-X of FIG. 9, of the distal part of the device shown on the previous figures.

Referring more particularly to FIGS. 7 and 9, we see that the gripping member 40 and the slide 42 comprise complementary means for locking to each other that can be activated at the end of the relative engagement movement.

These complementary locking means comprise, for example, as shown on FIGS. 7 and 9, the pair of coupling lugs 56 and a pair of locking windows 64, diametrically opposed relative to the axis X, formed in the proximal part 40P of the gripping member 40. These locking windows 64 are adjacent to the distal coupling gadroon 60. Thus, at the end of the relative engagement movement, the coupling lugs 56 of the slide 42 clip into the locking windows 64 of the gripping member 40 after crossing the hard point formed by the distal coupling gadroon 60.

Obviously, as an alternative, there could be only one clipping lug 56 or more than two clipping lugs 56 and a single locking window 64 or more than two locking windows 64.

Figure 6:
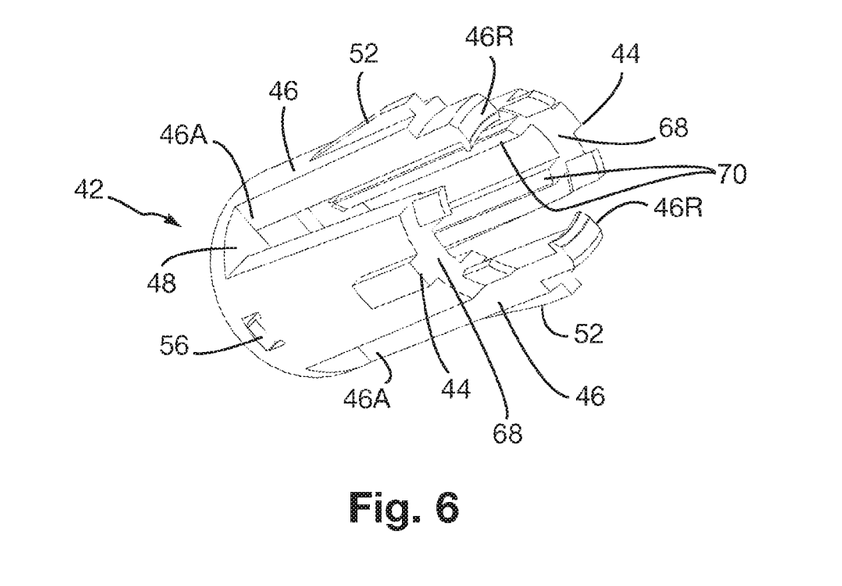
FIG. 6 is a perspective view of a slide mounted in the protective cap removal device illustrated on FIG. 5.

Referring more particularly to FIGS. 6 and 7, we see that the support 34 and the slide 42 comprise complementary stops 66, 68 for positioning each extractor 46 in its reference configuration retracted relative to the protective cap 32.

Referring more particularly to FIGS. 5 and 6, we see that the slide 42 comprises inner axial projections 70 for centering the protective cap 32 in the slide 42.

We will now describe the main steps of assembling the injection assembly 22 according to the first embodiment.

Initially, the support 34 of the injection syringe 26 and the removal device 36 are assembled separately.

To assemble the removal device 36, the slide 42 is inserted in the generally sleeve-shaped proximal part 40P of the gripping member 40. The coupling lugs 56 of the slide 42 cross the hard point formed by the proximal coupling gadroon 58 and are inserted axially between this proximal coupling gadroon 58 and the distal coupling gadroon 60. The gripping member 40 and the slide 42 are then coupled to each other in order to allow a relative translation movement, corresponding to the relative engagement movement, whose axial amplitude is limited by the axial distance between the proximal 58 and distal 60 coupling gadroons.

Figure 2:
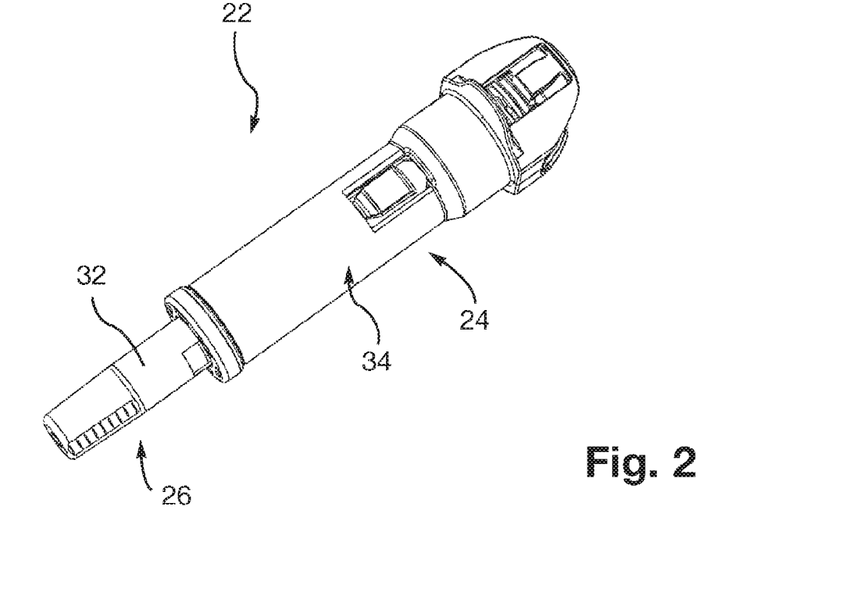

Then, according to a first method for assembling the injection assembly 22, the injection syringe 26 fitted with the protective cap 32 covering the injection needle 30 of the syringe is placed in the support 34 of the injection syringe 26, as shown on FIG. 2.

Then, the removal device 36 is placed around the protective cap 32 by inserting the slide 42 on the protective cap 32 by relative axial displacement parallel to the axis X, until the complementary positioning stops 66, 68 cooperate with each other, as shown on FIGS. 3 and 7.

Each extractor 46 is then in its reference configuration retracted relative to the protective cap 32, as shown on FIG. 8.

Note that, according to a second method for assembling the injection assembly 22, the injection syringe 26 can be placed in the support 34, not at the time described above, but when the removal device 36 is in the position shown on FIGS. 3, 7 and 8. The extractors 46 are in fact each in their reference configuration retracted relative to the protective cap 32, allowing this protective cap 32 to pass between the extractors 46.

Since the slide 42 abuts against the support 34 of the injection syringe 26, the gripping member 40 continues to move axially parallel to the axis X in the direction of the arrow A shown on FIG. 8.

Since the first 50 and second 52 complementary control members for controlling each extractor 46 are carried respectively by the gripping member 40 and by this extractor 46, the continuing movement of the gripping member 40 in the direction of the arrow A produces the relative engagement movement. Thus, since the first 50 and second 52 complementary control members for controlling each extractor 46 are cooperating with each other by ramp effect, each extractor 46 moves from its retracted reference configuration, shown on FIG. 8, to its cooperation configuration cooperating with the protective cap 32, shown on FIG. 10.

Note that the force exerted by ramp effect on each extractor 46 is applied, according to the distribution of forces in a class three lever, between the resistance end 46R and the support end 46A of the extractor 46.

In addition, at the end of the relative engagement movement, the coupling lugs 56 cross the hard point formed by the distal coupling gadroon 60 and clip into the locking windows 64 in order to lock the gripping member 40 and the slide 42 to each other, as shown on FIGS. 1 and 9.

The removal device 36 is then connected to the support 34 of the injection syringe 26. The hooks forming the resistance ends 46R of the extractors 46 are in fact engaged with the proximal end edge 32P of the protective cap 32, the removal device 36 being held on the support 34 of the injection syringe 26 by the frictional forces keeping the protective cap 32 inserted on the complementary part 28A of the syringe body 28.

When a user wants to use the injection assembly 22, he takes it in the configuration shown on FIG. 1, then pulls the gripping member 40 in the direction of the arrow R shown on this FIG. 1, applying to this gripping member 40 a force sufficient to overcome the frictional forces keeping the protective cap 32 inserted on the complementary part 28A of the syringe body 28.

This maneuvering movement applied by the user to the gripping member 40 pulls the slide 42, which is locked to this gripping member 40, as well as the protective cap 32 which is pulled by the extractors 46.

Figure 4:
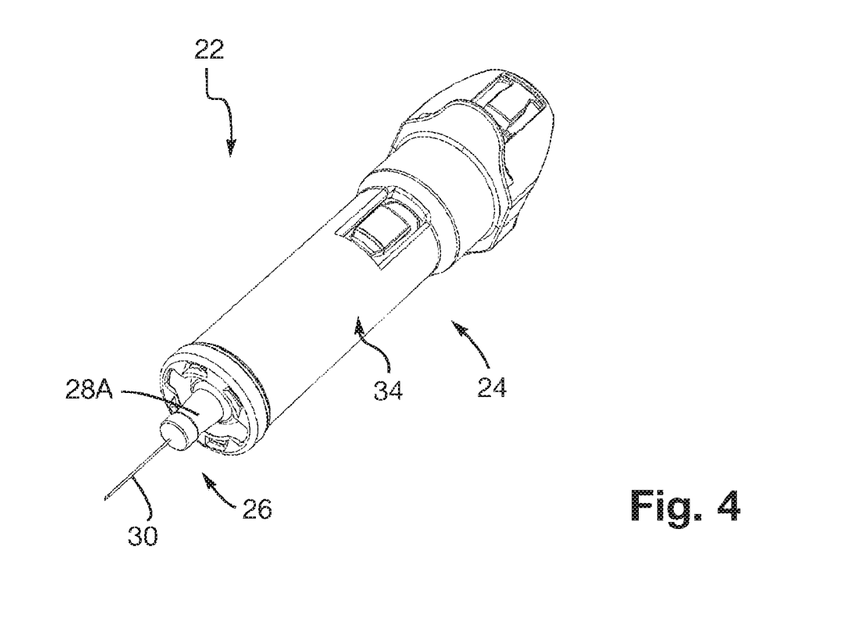

At the end of this maneuvering movement, the protective cap 32 is completely separated from the injection needle 30, the injection assembly 22 being in the configuration shown on FIG. 4.

We will now describe, referring to FIGS. 11 to 20, an injection assembly 22 comprising an assistance device for assisting in the operation of an injection syringe 26, according to a second embodiment of the invention. As in the previous figures, the injection assembly 22 has a very general shape of revolution about the axis X.

On these FIGS. 11 to 20, the elements similar to those of the previous figures are designated by the same references.

Figure 14:
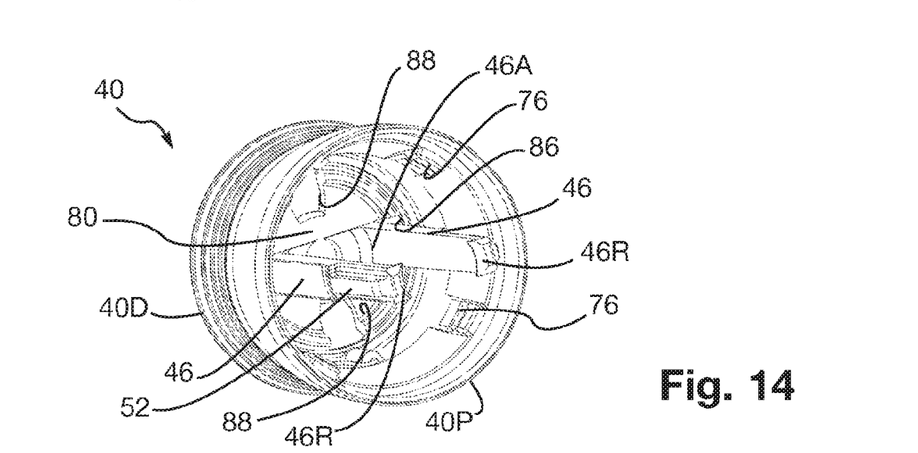
FIGS. 14 and 15 are perspective views showing respectively a gripping member and a member for maneuvering a protective cap removal device fitted to the assistance device according to the second embodiment of the invention.
Figure 15:
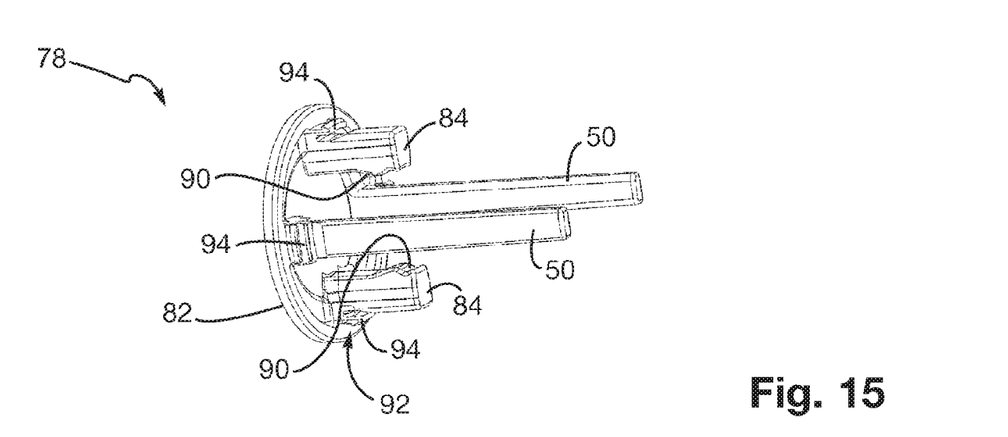
Figure 16:
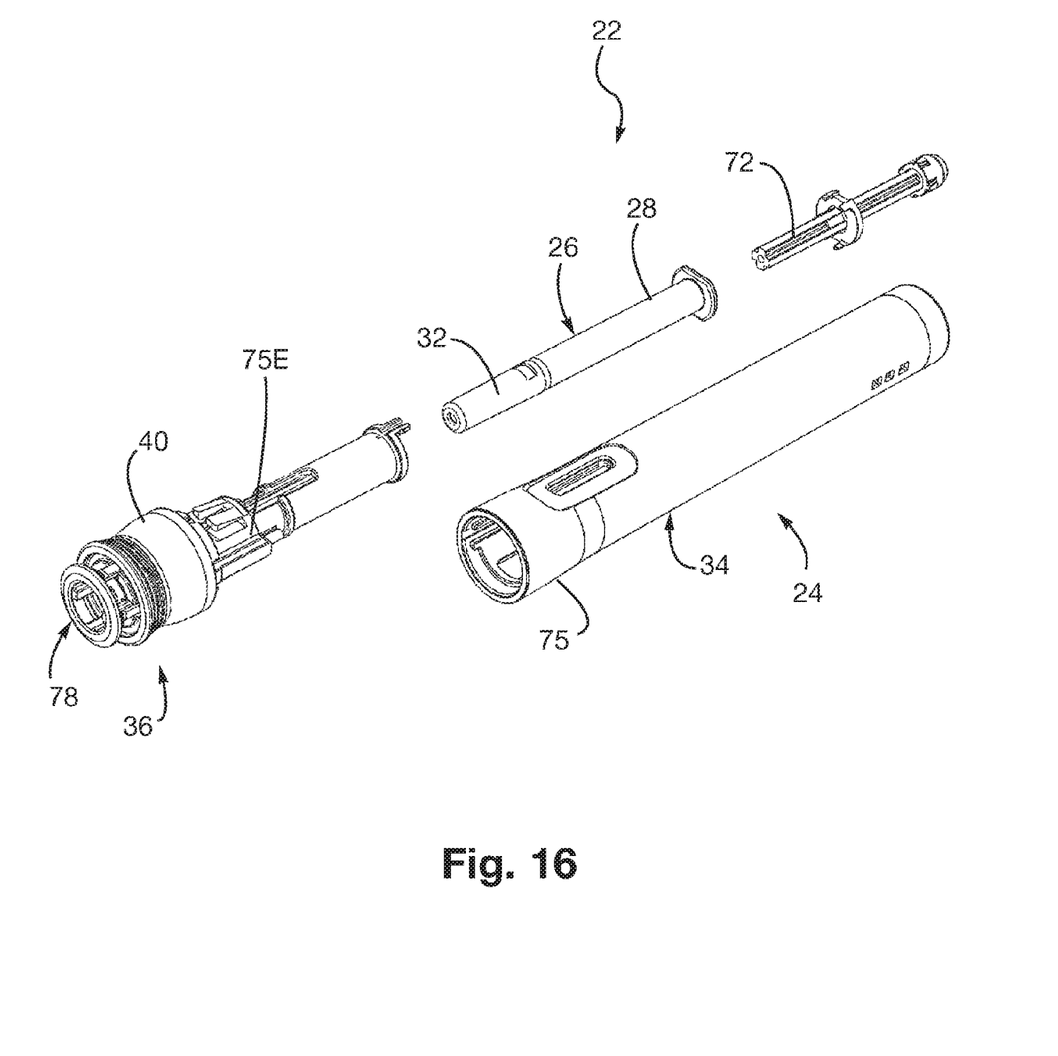
FIG. 16 is an exploded perspective view of a protective cap removal device fitted to the assistance device for assisting in the operation of an injection syringe according to the second embodiment of the invention.

The injection assembly 22 shown on FIGS. 11 to 20 comprises an injection syringe 26, shown in particular on FIGS. 16 to 20, similar to that described previously, housed in the assistance device 24 according to the second embodiment of the invention. FIG. 16 shows a rod 72 for maneuvering a piston 74. This piston 74, shown on FIGS. 17 to 20, is housed in the syringe body 28 so as to define the chamber 73 containing the medication to be injected.

Firstly, the assistance device 24 according to the second embodiment prevents or limits accidents when handling the injection syringe 26, by automatically masking the injection needle 30 of the injection syringe 26, just after the injection. Secondly, this assistance device 24 according to the second embodiment automates some of the syringe 26 operation steps, especially insertion of the injection needle 30 of the injection syringe 26 into the body of a patient and the distal displacement of the piston 74 of the injection syringe 26 into the body 28 of this injection syringe 26.

The syringe support 34 of the assistance device 24 according to the second embodiment comprises an outer body 75 of generally tubular shape and an end sleeve 75E projecting from one end of this outer body 75.

As in the first embodiment, the removal device 36 for removing the protective cap 32 is removably connected to the syringe support 34.

Figure 20:
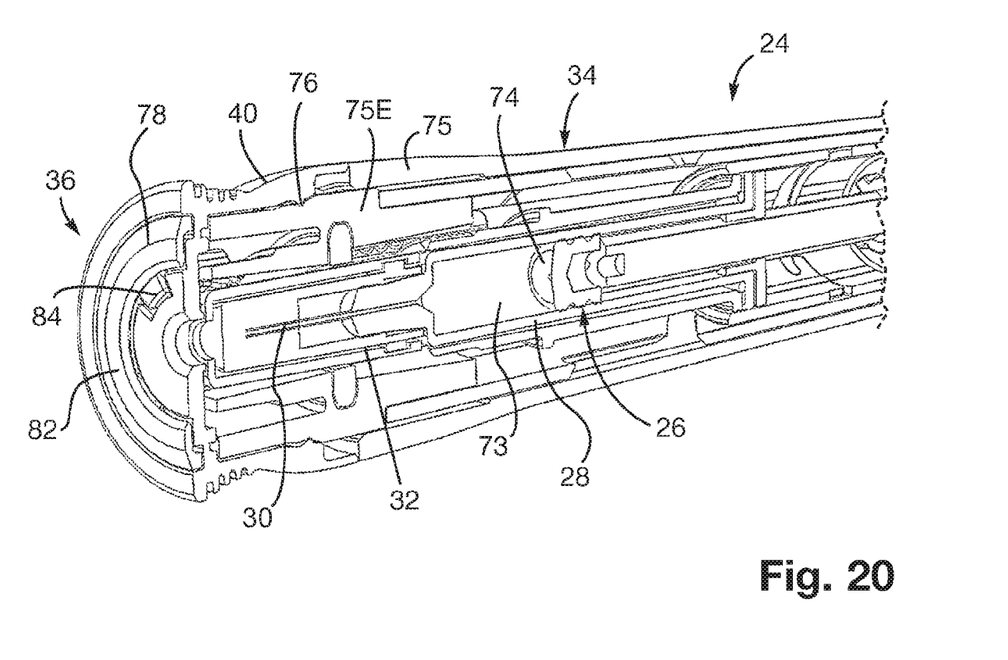

Thus, in the second embodiment, the gripping member 40 and the syringe support 34 comprise complementary means 76 for locking to each other, shown in particular on FIG. 20, that can be released when starting the maneuvering movement applied by the user to the gripping member 40 in order to remove the protective cap 32 from the injection needle 30.

The complementary locking means 76 consist, for example, of complementary clipping means formed on the gripping member 40 and the end sleeve 75E.

As in the first embodiment, the removal device 36 comprises the gripping member 40. In the second embodiment, however, unlike the first embodiment, each extractor 46 is attached to the gripping member 40, as shown in particular on FIG. 14.

More particularly, the gripping member 40 comprises two substantially parallel extractors 46, intended to cooperate with the protective cap 32 when removing this protective cap 32. As an alternative, the gripping member 40 could comprise only a single extractor 46 or more than two extractors 46.

In addition, the removal device 36 according to the second embodiment comprises a maneuvering member 78 (see in particular FIG. 15) mounted slidably in translation, substantially parallel to the axis X, in the gripping member 40.

Like the gripping member 40, the maneuvering member 78 is preferably made of plastic.

Figure 11:
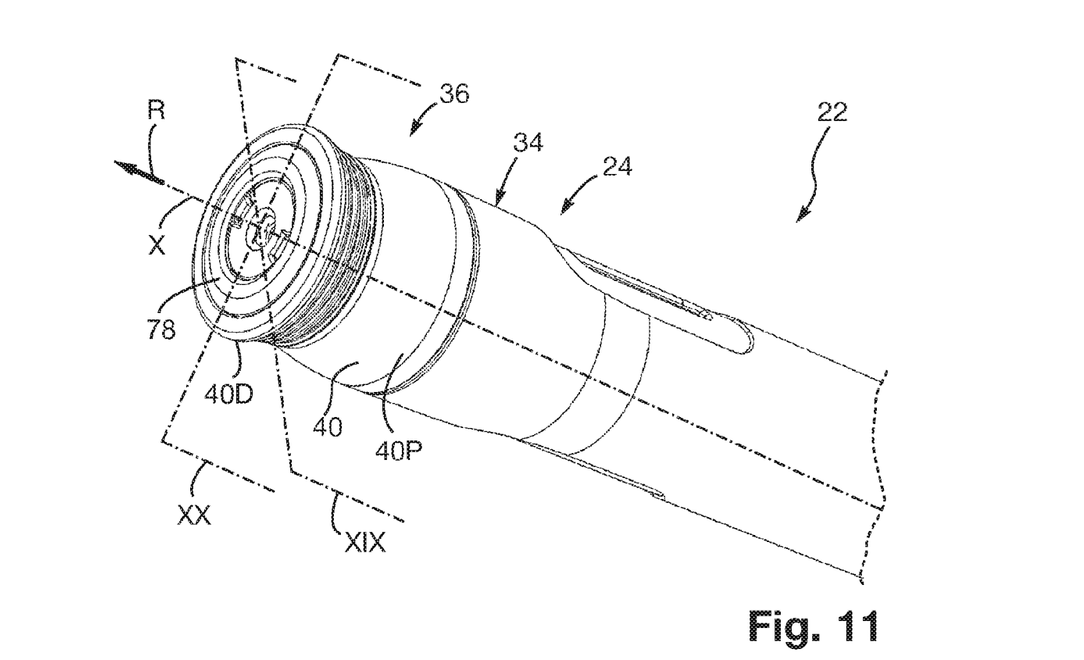
FIGS. 11 to 13 are perspective views of an injection assembly comprising an assistance device for assisting in the operation of an injection syringe according to a second embodiment of the invention, in various use or assembly configurations.

The maneuvering movement applied by the user to the gripping member 40 in order to remove the protective cap 32 from the injection needle 30 is similar to the maneuvering movement described concerning the first embodiment of the invention (see the arrow R on FIG. 11).

Referring in particular to FIGS. 11 to 14, we see that the gripping member 40 comprises, as in the first embodiment, a proximal part 40P, extended by a distal head 40D whose outer surface flares in the proximal to distal direction.

As in the first embodiment of the invention, each extractor 46 consists of an elastic arm extending substantially longitudinally in the proximal part 40P of the gripping member 40.

The maneuvering member 78 is mounted slidably in translation through a base 80 forming a distal end of the distal head 40D of the gripping member 40.

As in the first embodiment, each extractor 46 consists of an elastic arm extending substantially longitudinally in the proximal part 40P of the gripping member 40.

Preferably, as in the first embodiment, each extractor 46 forms a class 3 lever deformable between the retracted reference configuration and the cooperation configuration. Thus, firstly, each extractor 46 is provided with a resistance end 46R, for example in the shape of a hook, intended to cooperate with a proximal end edge 32P of the protective cap 32. As an alternative, the resistance end 46R of each extractor 46 could cooperate with another surface of the protective cap 32. Secondly, each extractor 46 is provided with a support end 46A, opposite the resistance end 46R, made in one piece with the base 80 of the gripping member 40 (see FIG. 14). Thus, the support ends 46A of the extractors 46 are connected to each other by the base 80 of the gripping member 40.

As in the first embodiment, the first 50 and second 52 complementary control members for controlling each extractor 46 cooperate with each other by ramp effect while executing their relative engagement movement. In the second embodiment, however, as shown in particular on FIGS. 13 to 15, for each extractor 46, the first control member 50 for controlling this extractor 46 is carried by the maneuvering member 78 and the second control member 52 for controlling this extractor 46 is attached in translation to the extractor 46.

Thus, referring in particular to FIGS. 14 and 15, we see that, for each extractor 46, the first control member consists of a longitudinal arm 50 attached to a ring 82 forming a distal end of the maneuvering member 78. The maneuvering member 78 therefore comprises two diametrically opposed and substantially parallel control members 50. In addition, for each extractor 46, the second control member consists of the radial projection 52 forming a ramp formed on the extractor 46.

Referring in particular to FIG. 15, we see that the maneuvering member 78 also comprises two pins 84 substantially parallel to each other and to the first control members 50, and attached to the ring 82. The alignment of the pins 84 is perpendicular to the alignment of the first control members 50.

Figure 17:
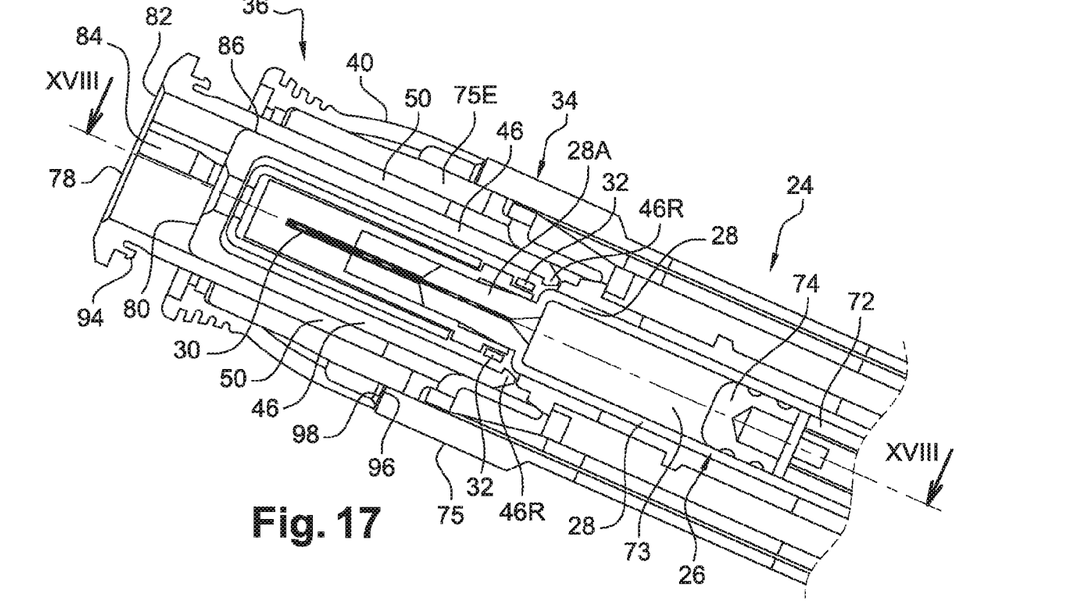
FIG. 17 is a cross-sectional view, along plane XVII of FIG. 12, of a distal part of the assistance device for assisting in the operation of an injection syringe according to the second embodiment of the invention.
Figure 18:
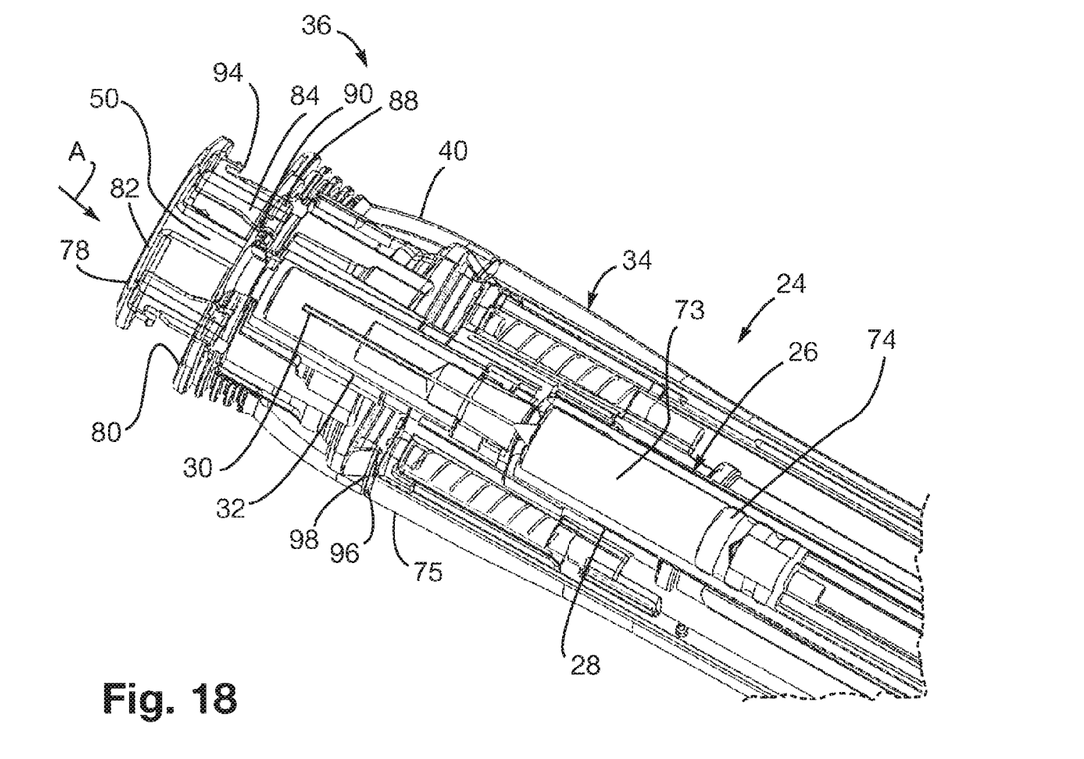
FIG. 18 is a cross-sectional view, along line XVIII-XVIII of FIG. 17, of the distal part of the assistance device for assisting in the operation of an injection syringe according to the second embodiment of the invention.

The first control members 50 and the pins 84 extend through holes 86, 88 formed in the base 80 of the gripping member 40 (see in particular FIGS. 14, 17 and 18). By cooperating with the contour of these holes 86, 88, the first control members 50 and the pins 84 are guided in translation in the gripping member 40.

Referring in particular to FIG. 18, we see that the gripping member 40 and the maneuvering member 78 comprise complementary means 90 for locking to each other that can be released when starting the relative engagement movement. These releasable complementary locking means 90 comprise, for example, complementary means with complementary recess and boss formed respectively on the pins 84 and the edges of the holes 88 for passing and guiding these pins 84.

Figure 19:
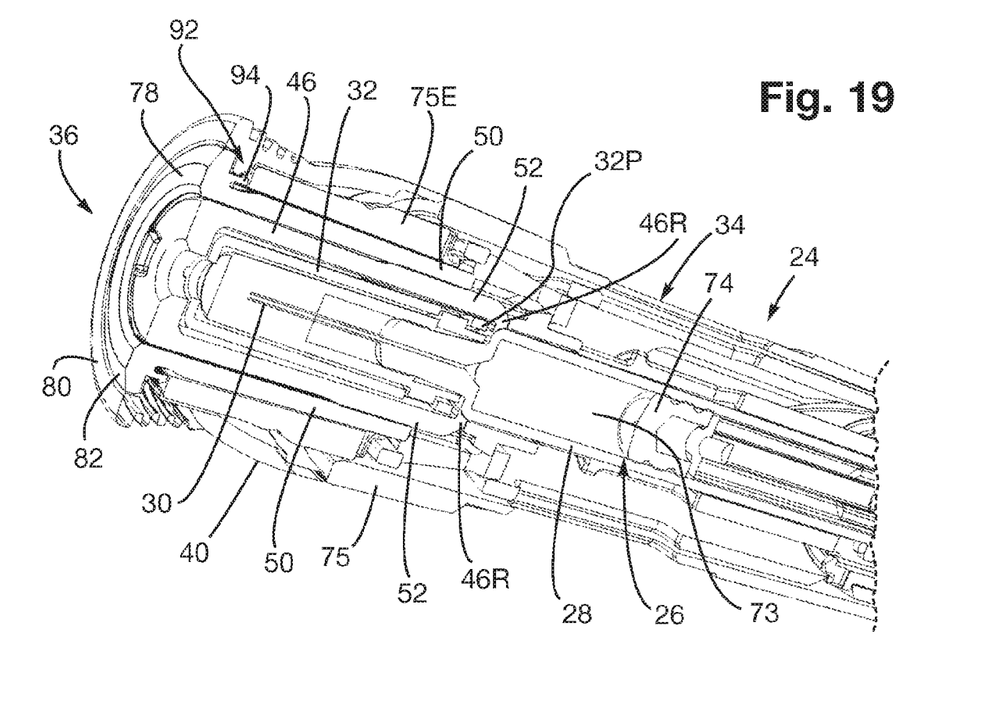
FIGS. 19 and 20 are cross-sectional views, respectively along planes XIX and XX of FIG. 11, of the distal part of the assistance device for assisting in the operation of an injection syringe according to the second embodiment of the invention.

Referring in particular to FIGS. 15 and 19, we see that the gripping member 40 and the maneuvering member 78 also comprise complementary means 92 for locking to each other that can be activated at the end of the relative engagement movement. These complementary locking means 92 comprise, for example, complementary clipping means formed respectively, firstly, on the ends for connecting with the ring 82 of the first control members 50 and of the pins 84 and, secondly, on the edges of the holes 86, 88 for passing and guiding the first control members 50 and the pins 84. FIGS. 15 and 19, in particular, show clipping hooks 94 attached to the ends for connection with the ring 82 of the first control members 50 and of the pins 84.

Referring more particularly to FIGS. 17 to 20, we see that the gripping member 40 and the syringe support 34 comprise complementary stops 96, 98 for positioning each extractor 46 in its reference configuration retracted relative to the cap 32.

More particularly, the stop 98 carried by the syringe support 34 to position an extractor 46 in its retracted reference position is formed on the end of the outer body 75 through which the end sleeve 75E projects.

We will now describe the possible steps of assembling the injection assembly 22 illustrated on FIGS. 11 to 20.

Thus, the removal device 36 can be assembled as follows. Initially, the maneuvering member 78 is placed in a distal position relative to the gripping member 40, then the first control members 50 and the pins 84 of the maneuvering device 78 are inserted in the gripping member 40, passing through the holes 86, 88 formed in this gripping member 40, until the releasable locking means 90 are activated. The maneuvering member 78 is then positioned relative to the gripping member 40 as shown in particular on FIGS. 12, 17 and 18.

Figure 12:
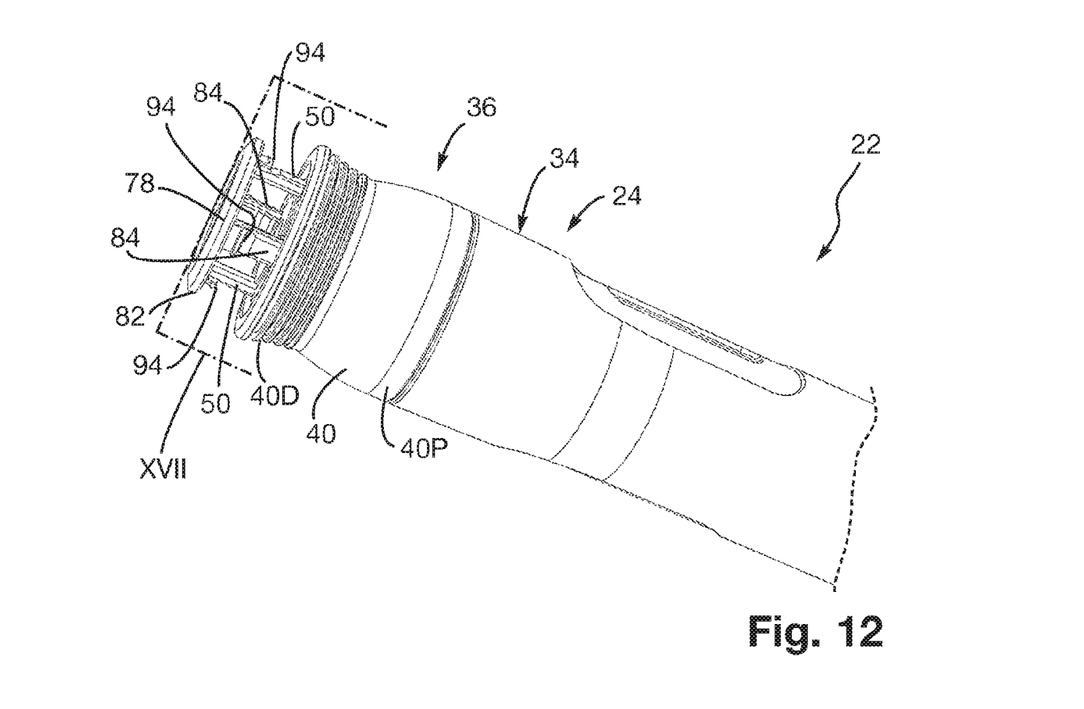

The gripping member 40 can then be inserted on the end sleeve 75E until the complementary locking means 76 are activated to lock the gripping member 40 and the syringe support 34 to each other, as shown in particular on FIGS. 12, 17 and 18.

The injection syringe 26 can be mounted in the support 34 before or after the previous step, depending on the assembly option chosen.

In addition, the gripping member 40 could also be assembled on the end sleeve 75E before assembling the maneuvering member 78 on the gripping member 40.

Once the configuration illustrated on FIGS. 17 and 18 has been obtained, the injection syringe 26 fitted with its protective cap 32 being housed in the syringe support 34, each extractor 46 is in its reference configuration retracted relative to the protective cap 32. The complementary positioning stops 96, 98 formed on the gripping member 40 and the end of the outer body 75 cooperate in fact with each other to ensure that the extractors 46 are in their reference configuration retracted relative to the protective cap 32.

The relative engagement movement is then performed by moving the maneuvering member 78 in the direction of the arrow A on FIG. 18. The ring 82 of the maneuvering member 78 is therefore pressed so as to release the releasable locking means 90 and insert the maneuvering member 78 further into the gripping sleeve 40.

Thus, since the first 50 and second 52 complementary control members for controlling each extractor 46 are cooperating with each other by ramp effect, each extractor 46 moves from its retracted reference configuration, shown on FIG. 17, to its cooperation configuration cooperating with the protective cap 32, shown on FIG. 18.

At the end of the relative engagement movement, the complementary locking means 92 are activated to lock the gripping member 40 and the maneuvering member 78 to each other, as shown on FIG. 19.

When a user wants to use the injection assembly 22 shown on FIGS. 11 to 20, he takes it in the configuration shown on FIG. 11, then pulls the gripping member 40 in the direction of the arrow R shown on this FIG. 11, applying to this gripping member 40 a force sufficient, firstly, to release the complementary locking means 76 locking the gripping member 40 and the end sleeve 75 of the syringe support 34 to each other and, secondly, to overcome the frictional forces keeping the protective cap 32 inserted on the complementary part 28A of the syringe body 28.

This maneuvering movement applied by the user to the gripping member 40 pulls the protective cap 32, which is pulled by the extractors 46.

Figure 13:
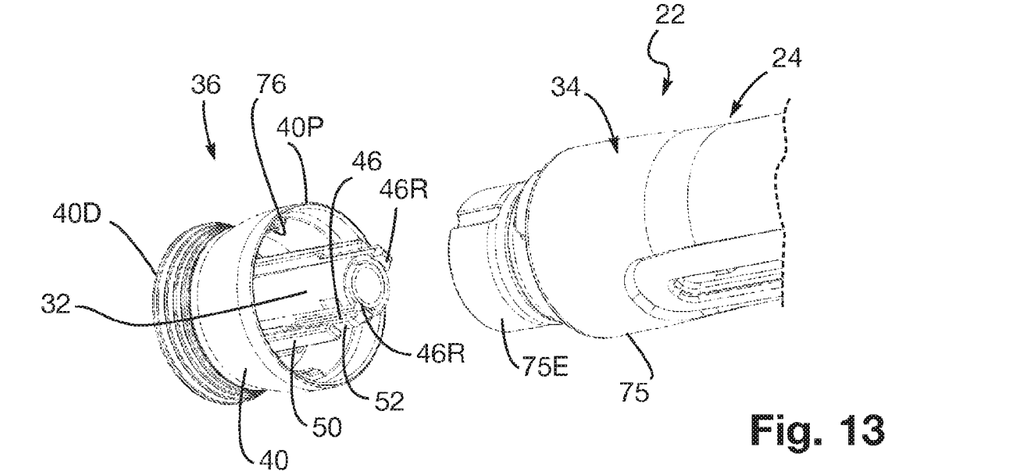

At the end of this maneuvering movement, the protective cap 32 is completely separated from the injection needle 30, the injection assembly 22 being in the configuration shown on FIG. 13.

Note that, as in the first embodiment, in this second embodiment, the relative engagement movement is independent of the maneuvering movement applied by the user to the gripping member 40 when removing the protective cap 32 from the injection needle 30.

The invention is not limited to the embodiments described and other embodiments will be clearly apparent to those skilled in the art. In particular, the injection syringe can be replaced by a cartridge provided with a needle.

The invention claimed is:

1. An assistance device for assisting in the operation of an injection syringe comprising a syringe body carrying an injection needle covered with a removable protective cap, the assistance device comprising:
    a syringe support in which the syringe body is intended to be housed, and
    a removal device for removing the protective cap removably connected to the syringe support, comprising:
    a gripping member, intended to be maneuvered by a user in order to remove this protective cap from the injection needle, and
    at least one extractor cooperating with the protective cap when removing the protective cap,
    wherein the removal device comprises first and second complementary control members for controlling the extractor which can be moved relative to each other in a relative cooperation movement, known as a relative engagement movement, in order to move the extractor between a reference configuration retracted relative to the protective cap, wherein the extractor is configured to be pulled away from the protective cap without exerting a withdrawal effort on the protective cap, and a cooperation configuration cooperating with the protective cap, wherein the extractor is configured to transfer to the protective cap a withdrawal effort applied to the extractor through the gripping member, the relative engagement movement being independent of the maneuvering movement applied by the user to the gripping member in order to remove the protective cap from the injection needle;
    wherein the extractor is attached to the gripping member and wherein the first control member for controlling the extractor is carried by a maneuvering member mounted slidably in translation in the gripping member and the second control member for controlling the extractor is attached in translation to the extractor.

2. The assistance device for assisting in the operation of the injection syringe according to claim 1, wherein the gripping member comprises a generally sleeve-shaped proximal part, the extractor consisting of an elastic arm extending substantially longitudinally in the proximal part and forming a class 3 lever deformable between the retracted reference and cooperation configurations, the extractor being provided with a resistance end, intended to cooperate with the protective cap.

3. The assistance device for assisting in the operation of the injection syringe according to claim 1, wherein the removal device comprises at least two extractors forming respectively two class 3 levers, substantially parallel to each other, these extractors each being provided with a resistance end, intended to cooperate with the protective cap, and a support end opposite the resistance end, the support ends of the extractors being connected together.

4. The assistance device for assisting in the operation of the injection syringe according to claim 1, wherein the maneuvering movement applied by the user to the gripping member in order to remove the protective cap from the injection needle comprises a translation, the relative engagement movement being parallel to this translation.

5. The assistance device for assisting in the operation of the injection syringe according to claim 1, wherein the first and second complementary control members for controlling the extractor comprise respective inclined portions forming ramps adapted to cooperate with each other by ramp effect under the effect of the relative engagement movement.

6. The assistance device for assisting in the operation of the injection syringe according to claim 1, wherein the gripping member and the syringe support comprise complementary stops for positioning the extractor in its reference configuration retracted relative to the protective cap.

7. The assistance device for assisting in the operation of the injection syringe according to claim 6, wherein the syringe support comprises an outer body of generally tubular shape and an end sleeve projecting from one end of this outer body,
    the stop carried by the syringe support to position the extractor in its reference configuration retracted relative to the protective cap being formed on the end of the outer body, and
    the complementary member for locking the gripping member and the syringe support being formed on the gripping member and the end sleeve.

8. The assistance device for assisting in the operation of the injection syringe according to claim 1, wherein the gripping member and the syringe support comprise complementary member for locking to each other that can be released when starting the maneuvering movement applied by the user to the gripping member in order to remove the protective cap from the injection needle.

9. The assistance device for assisting in the operation of the injection syringe according to claim 1, wherein the gripping member and the maneuvering member carrying the first control member for controlling the extractor comprise complementary locking members for locking the gripping member and the maneuvering member to each other, wherein the complimentary locking members can be released when starting the relative engagement movement.

10. The assistance device for assisting in the operation of the injection syringe according to claim 1, wherein the gripping member and the maneuvering member carrying the first control member for controlling the extractor comprise complementary locking members for locking the gripping member and the maneuvering member to each other, wherein the complimentary locking members can be activated at the end of the relative engagement movement.

11. An injection assembly comprising an assistance device for assisting in the operation of an injection syringe and an injection syringe housed in this assistance device, wherein the assistance device for assisting in the operation of the injection syringe is according to claim 1.

* * * * *